United States Patent [19]

Storz

[11] 3,957,252

[45] May 18, 1976

[54] APPARATUS FOR CLEANING MEDICAL INSTRUMENTS

[75] Inventor: Karl Storz, Tuttlingen, Germany

[73] Assignee: Storz-Endoskop GmbH, Schaffhausen, Switzerland

[22] Filed: June 17, 1974

[21] Appl. No.: 479,822

[30] Foreign Application Priority Data
Nov. 7, 1973 Switzerland.................... 15629/73
Apr. 30, 1974 Switzerland.................... 5928/74

[52] U.S. Cl................................. 259/1 R; 134/1; 134/184; 259/DIG. 41
[51] Int. Cl.²........................................ B01F 11/02
[58] Field of Search................ 4/260; 134/1, 184; 259/1 R, DIG. 41; 68/3 SS

[56] References Cited
UNITED STATES PATENTS

| | | | |
|---|---|---|---|
| 2,884,650 | 5/1959 | Cooper | 4/206 |
| 3,445,092 | 5/1969 | Fierle | 134/184 X |
| 3,572,995 | 3/1971 | Martin | 134/1 X |

FOREIGN PATENTS OR APPLICATIONS

| | | | |
|---|---|---|---|
| 1,102,562 | 5/1955 | France | 134/184 |

Primary Examiner—Stanley N. Gilreath
Assistant Examiner—Alan Cantor
Attorney, Agent, or Firm—Oliver D. Olson

[57] ABSTRACT

Support means is provided for mounting an ultrasonic oscillator for engaging washing water in a conventional sink, for use in cleaning medical instruments. One form of support means is an overflow pipe adapted to be inserted at its lower end in the drain opening of a conventional sink and stabilized at its upper end by an arm extended pivotally from the oscillator power supply control positioned adjacent the sink, the oscillator being mounted on the upper end of the overflow pipe and the overflow pipe having a water inlet opening intermediate its ends for establishing the maximum level of washing water in the sink. Another form of support means is a float structure adapted to float on washing water contained in a conventional sink, the float structure mounting an ultrasonic oscillator for engaging the washing water.

2 Claims, 2 Drawing Figures

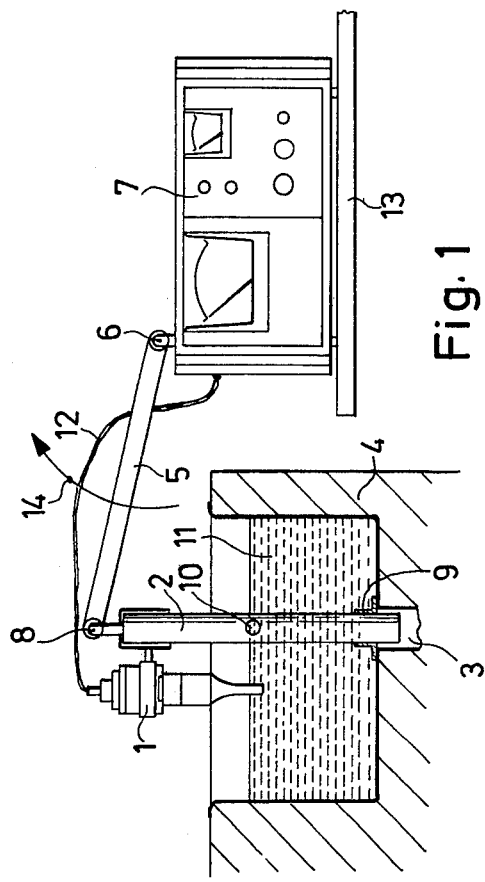
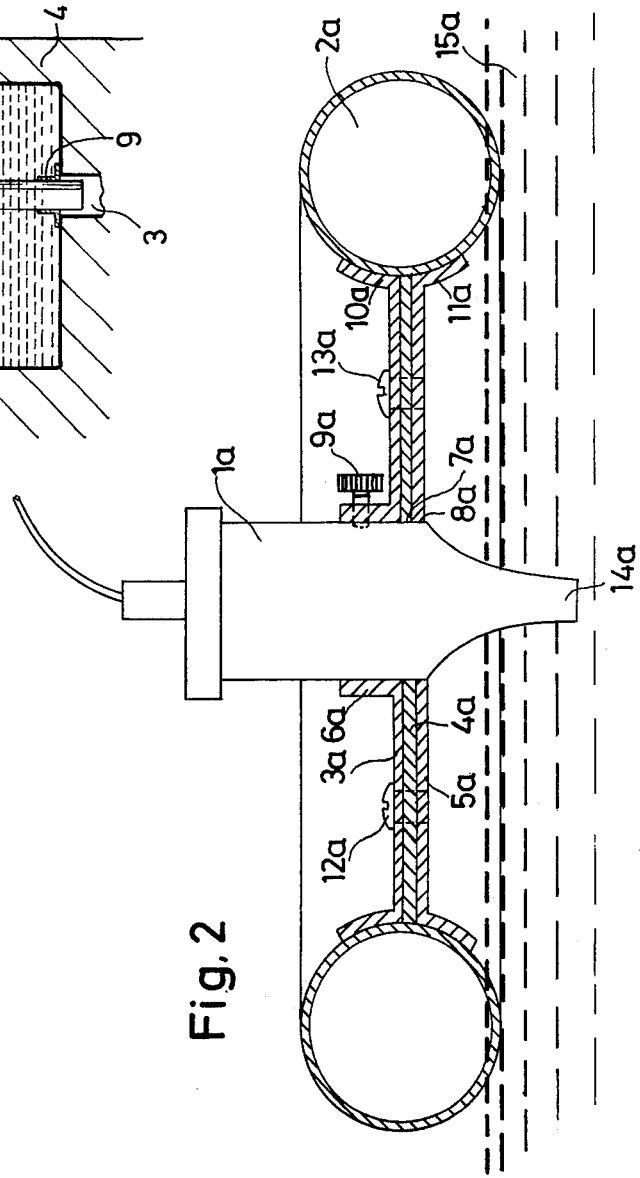

APPARATUS FOR CLEANING MEDICAL INSTRUMENTS

The invention relates to an apparatus for cleaning medical instruments, particularly endoscopes with an ultrasonic oscillator.

Ultrasonic oscillators of this type are already known, but their use in hospitals and medical practices has been limited because hitherto it was considered necessary to install special ultrasonic cleaning tanks requiring considerable structural changes. Furthermore, the additional space requirements have also worked against the installation of the known ultrasonic cleaning tanks because the sinks which form part of the normal equipment are still necessary when using the known ultrasonic cleaning equipment.

The problem of the invention is therefore to so improve the apparatus of the type indicated hereinbefore that it can be used for cleaning medical instruments quite independently of special ultrasonic cleaning tanks.

According to the invention this problem is solved in that the ultrasonic oscillator is arranged in easily removable manner on the surface of the washing water in any random sink. Therefore it can be used in any standard existing sink which is necessary for washing hands. As a result the apparatus is not only much less costly, but in particular a great deal of space is saved as compared with that required for the special ultrasonic tank according to the prior art. It is important in this connection that the apparatus according to the invention can be removably installed, repeatedly in the sink, extremely rapidly with only a single manipulation.

Therefore according to a further development of the invention the ultrasonic oscillator is arranged on an overflow pipe which can be inserted in the drain of a sink, whereby a mounting is provided permitting the installation of the apparatus in easily removable manner in the sink. Consequently, the overflow pipe togther with the ultrasonic oscillator can be very rapidly and easily pivoted into the sink and after cleaning the instruments can be equally rapidly and easily pivoted out of the same.

It is advantageous in this connection for an articulation to be positioned on a switch-box which is in general required for an ultrasonic oscillator in any case. Thus, it is not necessary to make any structural changes even to the outside of the sink because the switch-box simultaneously forms part of the mounting according to the invention.

However, there are also sinks wherein there is either no overflow pipe or wherein the overflow pipe cannot be used for this purpose.

Therefore, according to another feature of the invention it is particularly preferred for the ultrasonic oscillator to be fixed to a floating member. Consequently, the floating ultrasonic oscillator is always at the correct distance from the surface of the water, and not only is the overflow pipe unnecessary but also the indicated mounting for the pivoting installation of the overflow pipe together with the ultrasonic oscillator becomes superfluous. This greatly simplifies the apparatus and enables it to be easily installed and removed again from any sink or similar washing vessel. As the weight of the ultrasonic oscillator is relatively small, it can be made to float without any particularly large floating member.

According to a further development of this feature, the floating member is circular and in the center of the ring plates are fixed to the floating member for receiving the ultrasonic oscillator. In this way the ultrasonic oscillator can be fitted very simply in the dead center of the circular floating member which virtually excludes an inclined position or the tipping over of the floating member.

Appropriately the ultrasonic oscillator is detachably fixed in a central flange of the uppermost disc plate and corresponding holes in the remaining disc plates. In this way the immersion depth of the oscillator can be easily adjusted by means of the screw without making the apparatus complicated.

Further advantages and details of the invention can be gathered from the following description of two embodiments with reference to the drawings, which show:

FIG. 1 is a schematic representation, partly in section, of a first embodiment;

FIG. 2 is a section through the second embodiment.

On the left-hand side of FIG. 1 can be seen the sink 4 with the drain 3 on a greatly reduced scale. In drain 3 is inserted an overflow pipe 2 with a securing flange 9 which further towards the top has the inlet 10 up to which the water 11 in the sink 4 has risen. According to the invention the top of overflow pipe 2 is connected with an ultrasonic oscillator 1 which projects into the washing water 11. In addition, the top of overflow pipe 2 is provided with an articulation 8 which is connected with an arm 5 whose other end is connected to a switchbox 7 by means of another articulation 6. An electric cable 12 leads from this switchbox 7 to oscillator 1. Switchbox 7 has the usual electrical instruments which are known per se and require no further explanation. The ultrasonic oscillator 1 is also known to the skilled expert and therefore requires no detailed explanation.

Switchbox 7 is placed in movable manner on table 13 or similar support whose height can be varied relative to the sink 4 due to the flexibility of the mounting.

FIG. 1 shows the position of use for cleaning medical instruments in washing water 11 which permits a particularly intense cleaning as a result of the ultrasonic oscillations. The invention makes it unnecessary to use a special ultrasonic cleaning vessel because the apparatus according to the invention can be easily and rapidly removed from the conventional sink 4.

To this end the mounting with arm 5 and the oscillator connected thereto, as well as the overflow pipe 2, are pivoted to the right in the direction of the arrow 14 in FIG. 1 and placed over the switchbox 7 towards the right-hand side. As a result the complete apparatus is moved out of the working area of the conventional sink 4 and this can be immediately used for other purposes, particularly in view of the fact that after removing overflow pipe 2 the water 11 immediately flows away through drain 3.

The invention therefore makes it possible to use any existing sink as an ultrasonic cleaning vessel. When a further ultrasonic cleaning operation is to be performed, it is extremely simple to pivot back the overflow pipe 2 together with the ultrasonic oscillator 1 and insert the same in drain 3, whereupon after allowing the water 11 to flow in, cleaning can immediately recommence. This can take place within a few seconds, particularly if switchbox 7 is left in this position. The mounting with pivot arm 5 and switchbox 7 or a similar support is necessary for keeping overflow pipe 2 together with oscillator 1 in this position.

The invention is not restricted to the represented embodiment but numerous other embodiments and particular mountings can be used within the scope of the invention. For example, the articulation 8 at the top of overflow pipe 2 can be eliminated, but this makes it necessary for the switchbox 7 or some corresponding support for articulation 6 to have a clearly defined height relative to sink 4. However, this could for example be compensated by telescopic displacement of overflow pipe 2.

It is also conceivable for overflow pipe 2 to be provided with inclined downwardly directed feet so that in this way a secure mounting in the sink is ensured. However, in this connection it would be necessary to take account of the fact that drain 3 is located at different points in different sinks, and that the feet could sometimes prove troublesome in washing water 11. Therefore the represented embodiment is preferred.

In this connection, it is also possible to provide more than two articulations 6 and 8 should the need arise.

In the center of FIG. 2 and not in section is shown the ultrasonic oscillator 1a whose end 14a is immersed in the washing water 15a. It is secured by the circular floating member 2a which can for example be constructed in circular manner around the ultrasonic oscillator 1a. However, the invention is not restricted to this shape of the floating member 2a. In the center of the circular floating member 2a are provided a plurality of sheet metal disc plates 3a, 4a, 5a which are held together by screws 12a and 13a. The upper disc plate 3a is provided with an outer flange 10a which rests on the floating member 2a and with an inner flange 6a which is constructed with a screw 9a for securing the ultrasonic oscillator 1a. The lower sheet metal disc plate 5a also has an outer flange 11a for fixing or securing the floating member 2a. Therefore, further attachment means for the floating member 2 a are not necessary because it is sufficient for the two flanges 10a and 11a to engage with member 2a.

The height of the ultrasonic oscillator 1a for changing its immersion depth can be easily adjusted by means of screw 9a, and after unscrewing screw 9a the oscillator can be easily removed from flange 6a.

In addition, it is obviously also possible to remove the complete apparatus from the sink 4 and then reinsert it without an overflow pipe or a pivotable mounting being necessary. In addition the apparatus is independent of the height of the washing water 15a. Therefore, it is possible to have a relatively low or a relatively high water level.

Having now described my invention and the manner in which it may be used, I claim:

1. Apparatus for cleaning medical instruments in a conventional sink having a drain opening, comprising:
    a. an elongated overflow pipe adapted for removable registry at its lower end with the drain opening of a sink and having an inlet opening intermediate its ends for defining the maximum level of water in a sink,
    b. an ultrasonic oscillator mounted on the upper end of the overflow pipe and projecting below the inlet opening therein for engaging washing water in a sink,
    c. a separate switch box for the oscillator adapted to be supported adjacent a sink,
    d. an elongated electric cable interconnecting the oscillator and switch box, and
    e. an elongated arm pivotally connected at one end to the switch box and at the opposite end to the oscillator.

2. The apparatus of claim 1 wherein the elongated overflow pipe is provided adjacent its lower end with a securing flange providing a liquid tight seal between the pipe and drain opening of a sink.

* * * * *